(12) United States Patent
Broadley et al.

(10) Patent No.: US 10,130,900 B2
(45) Date of Patent: Nov. 20, 2018

(54) COMPOSITE COLUMN FOR USE IN HIGH PRESSURE LIQUID CHROMATOGRAPHY

(71) Applicant: Lake Region Manufacturing, Inc., Chaska, MN (US)

(72) Inventors: Mark W. Broadley, Downingtown, PA (US); John K. Eckert, Boyertown, PA (US)

(73) Assignee: Bandera Acquisition, LLC, Foxborough, MA (US)

(*) Notice: Subject to any disclaimer, the term of this patent is extended or adjusted under 35 U.S.C. 154(b) by 0 days.

(21) Appl. No.: 15/624,903

(22) Filed: Jun. 16, 2017

(65) Prior Publication Data
US 2017/0361246 A1    Dec. 21, 2017

Related U.S. Application Data

(60) Provisional application No. 62/350,769, filed on Jun. 16, 2016.

(51) Int. Cl.
*B01D 15/22*    (2006.01)
*B21C 1/24*    (2006.01)
(Continued)

(52) U.S. Cl.
CPC ............. *B01D 15/22* (2013.01); *B01D 15/10* (2013.01); *B21C 1/16* (2013.01); *B21C 1/24* (2013.01);
(Continued)

(58) Field of Classification Search
CPC ........ B01D 15/14; B01D 15/22; B01D 15/10; B21C 1/16; B21C 1/24; F16L 9/14;
(Continued)

(56) References Cited

U.S. PATENT DOCUMENTS 3,238,759 A    3/1966    Ness
4,070,285 A    1/1978    Abrahams
(Continued)

FOREIGN PATENT DOCUMENTS

WO    2004018990    3/2004
WO    2009088663    7/2009
WO    2013032832    3/2013

OTHER PUBLICATIONS

Bohn, "What's the difference between 304 and 316 stainless steel", Nema Enclosures. Sep. 27, 2012.*
(Continued)

*Primary Examiner* — Katherine Zalasky
*Assistant Examiner* — Benjamin L Lebron
(74) *Attorney, Agent, or Firm* — Grossman, Tucker, Perreault & Pfleger, PLLC

(57) ABSTRACT

A multi-walled tube that is useful as an analytical column in which chemical mixtures can be separated into their individual components is described. In order to be acceptable as an analytical column, the inner surface of the multi-walled tube must support effective separation, but not react chemically with or contaminate the solvent or the analyte (sample to be separated). Grade 316 stainless steel is typically preferred for this purpose. Moreover, the inner diameter (ID) surface of the multi-walled column is preferably very smooth (less than 10 micro inch Ra) with no interruptions in the surface such as scratches, pits, or asperities. However, since the column is designed to be attached to chromatographic equipment using standard size connection features, the size of standard fittings define the outer diameter (OD) of the column.

28 Claims, 4 Drawing Sheets

(51) Int. Cl.
  *G01N 30/60* (2006.01)
  *F16L 9/14* (2006.01)
  *B01D 15/10* (2006.01)
  *B21C 1/16* (2006.01)
  *G01N 30/32* (2006.01)

(52) U.S. Cl.
  CPC ................ *F16L 9/14* (2013.01); *G01N 30/60* (2013.01); *G01N 30/6052* (2013.01); *G01N 30/6073* (2013.01); *G01N 30/32* (2013.01); *G01N 30/6026* (2013.01); *G01N 30/6095* (2013.01)

(58) Field of Classification Search
  CPC ............. G01N 30/6091; G01N 30/603; G01N 30/6026; G01N 30/6039; G01N 30/6004; G01N 30/6052; G01N 30/32; G01N 30/60; G01N 30/6073; G01N 30/6095
  See application file for complete search history.

(56) References Cited

U.S. PATENT DOCUMENTS

| | | | |
|---|---|---|---|
| 4,125,924 A | 11/1978 | Kennedy et al. | |
| 5,467,631 A | 11/1995 | Eberts et al. | |
| 5,614,089 A * | 3/1997 | Allington | B01D 11/0203 210/198.2 |
| 5,858,556 A | 1/1999 | Eckert et al. | |
| 5,881,592 A | 3/1999 | Blackwell et al. | |
| 7,861,571 B1 | 1/2011 | Giaimo et al. | |
| 9,089,794 B2 | 7/2015 | Lundin et al. | |
| 2004/0035774 A1* | 2/2004 | Horsman | B01D 15/22 210/198.2 |
| 2004/0234575 A1 | 11/2004 | Horres et al. | |
| 2011/0278214 A1* | 11/2011 | Benevides | B01D 15/22 210/198.2 |
| 2012/0037555 A1* | 2/2012 | Lundin | B01D 15/22 210/198.2 |
| 2014/0158599 A1* | 6/2014 | Michienzi | G01N 30/6052 210/198.2 |

OTHER PUBLICATIONS

Shaheen, L. "Tube drawing principles". Retrieved from https://www.thefabricator.com/article/tubepipeproduction/tube-drawing-principles. Mar. 13, 2007.*
17-7 PH Stainless Steel Tubing, http://www.americantube.com:80/17-7-series.html.
Extended European Search, Application No. 17176505.0, dated Oct. 20, 2017.

* cited by examiner

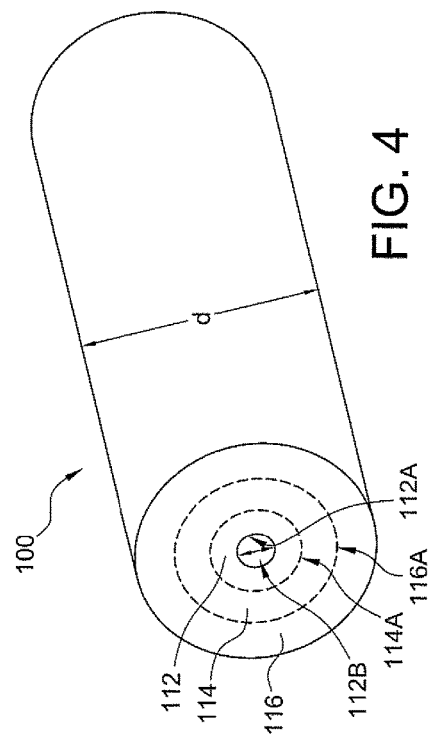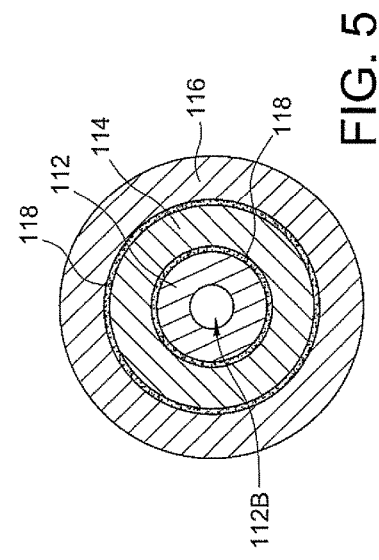

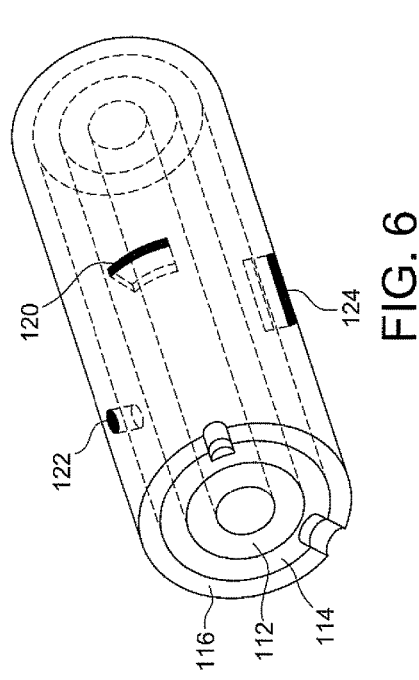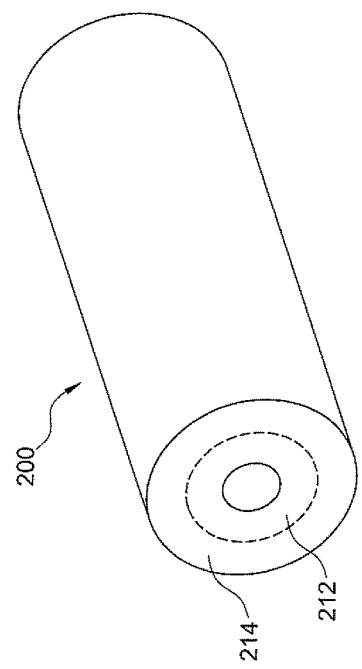

COMPOSITE COLUMN FOR USE IN HIGH PRESSURE LIQUID CHROMATOGRAPHY

CROSS-REFERENCE TO RELATED APPLICATION

This application claims priority to U.S. provisional patent application Ser. No. 62/350,769, filed on Jun. 16, 2016.

BACKGROUND OF THE INVENTION

1. Field of the Invention

The present invention generally relates to the field of multi-layer composite tubes and in particular, composite tubes that are designed as high pressure liquid chromatography (HPLC) columns intended for use in analytical separation of molecular mixtures. The present invention provides columns having an inner diameter (ID) that is smaller than conventionally made monolithic drawn chromatography columns. Columns of the present invention have a multi-tubular structure with only the inner tube being of a high value, corrosion resistant material. That is in contrast to a monolithic column made from the same high value material. Manufacturing the entire column from a high value material significantly increases the cost of the column. The present invention also provides chromatography columns that are inherently free of internal surface defects that often occur when drawing a monolithic tube with a very thick wall.

2. Prior Art

Analytical HPLC chromatography is used to separate and analyze the molecular chemistry within a sample of mixed molecules. The chromatography column is the component in the chromatographic equipment where separation of molecules within the sample occurs. The column is prepared in advance of the chromatography process by packing its lumen with very small spheres of solid media (stationary phase). The stationary media is characterized as having various surface chemistries designed to interact with a specific analyte to facilitate separation during the analytical chromatography process. Packing the stationary media into the column lumen is done using hydrostatic pressures of up to 30,000 psi. Of note, liquid pressures during the analytical separation process can exceed 20,000 psi. During the analytical chromatography process, the chromatography column contains both the stationary media and the flowing liquid sample (mobile phase) consisting of a solvent and analyte.

The chromatography industry is trending to smaller size samples and greater analytical precision (selectivity). This is driving chromatography columns to smaller inner diameter (ID) sizes. However, the columns must have standard size connection features, such as threaded fittings, configured for connection to the pressurized sample flow path of the chromatographic equipment. The size of the standard fitting defines the outer diameter (OD) of the column and the desired separation volume and selectivity define the inner tubular diameter (ID).

Once the inner and outer tubular geometries are established, the very high packing pressures inherent to analytical HPLC chromatography define the required pressure rating of the column. The pressure rating is a function of the OD size, wall thickness (WT) and column material strength.

The trend to smaller column ID sizes at a constant OD size results in thick wall column geometries with low OD to wall thickness ratios, preferably less than 3:1 (<3). These geometries are difficult to draw as a monolithic tube using conventional tube drawing methods. Moreover, prior art monolithic tubes having low OD to wall thickness ratios are prone to linear defects on the ID surface. A tube having linear defects severely reduces the selectivity of the chromatography column by allowing the liquid or mobile phase to flow through the linear defects, bypassing the stationary phase and increasing the sample peak width at the detector.

Therefore, there is a need for an improved high pressure liquid chromatography column that meets the industry demand for smaller ID sizes (less than 1.5 mm), but has standard fittings for connection to conventional chromatography equipment.

There is also a need for an improved high pressure liquid chromatography column having an ID surface that is substantially free of linear defects that would otherwise be significant enough to allow the liquid or mobile phase to bypass the stationary media.

Further, there is a need for an improved high pressure liquid chromatography column made of a desired high value material that offers improved ID surface chemical compatibility, matching the requirements of many different solvents and analytes, but without the high cost of a monolithic column made from the same high value material.

Moreover, there is a further need for an improved high pressure liquid chromatography column made from materials that offer improved hydrostatic pressure resistance, yet have acceptable outer diameter corrosion resistance and inner diameter surface chemical compatibility.

SUMMARY OF THE INVENTION

Thus, the present invention relates to a composite tubular assembly that is useful as a high pressure liquid chromatography (HPLC) column and method for making such a column. The HPLC column utilizes different tubular materials arranged in multiple tubular layers. The materials in each tube can be independently selected to perform the function required of that layer. In addition, the relative tubular thickness of any one the tube can be designed so that no more material than required for each tube to perform its intended function is used. This lowers the overall cost of the column when high value materials are required to achieve at least one of the layer functions, for example the inner tube that will contact the stationary media and in use the liquid or mobile phase comprising the solvent and analyte.

Furthermore, the reduced wall thickness of each of the tubular layers allows for the use of tube manufacturing processes that differ significantly from those required to make a conventional monolithic tube having similarly sized inner and outer diameters. For instance, the relatively thin-walled inner tube of the present composite tubular assembly has a sufficiently high outer diameter to wall thickness (OD:WT) ratio and provides a chemically compatible surface that can be drawn by a process that is inherently resistant to the formation of linear defects that often occur on the ID of thick wall drawn tubes.

The present invention also describes various methods for making a composite tubular assembly that is useful as an HPLC column. For example, in a three-tube column, the manufacturing process includes selecting the materials required to perform the various functions of the inner, middle and outer tubular layers. Then, the tubes are individually manufactured using the appropriate tube drawing process that is most suitable for their function. This is followed by assembly and cinching steps where the inner, middle and outer tubes are assembled into a single composite tubular assembly, and then reduced in diameter by cinching to eliminate clearance between the tubular layers. Optionally heat treating and/or conditioning steps can be used to finish the tubular assembly.

Thus, a generic process according to the present invention includes the steps of:

1. Selecting materials that are appropriate for the inner, middle and outer tubular layers;
2. Preparing the respective tubular layers;
3. Joining the tubular layers into a composite tubular assembly that is suitable for use as a high pressure liquid chromatography column;
4. Optionally heat treating the tubular assembly; and
5. Optionally conditioning the inner surface of the inner tubular layer.

These and other objects of the present invention will become increasingly more apparent to those skilled in the art by reference to the following detailed description and the appended drawings.

BRIEF DESCRIPTION OF THE DRAWINGS

FIG. 4 is a perspective view showing a three-layer tubular assembly 100 according to the present invention.

FIG. 5 is a cross-sectional view showing the inner, middle and outer tubes 112, 114 and 116 connected together using a heat-curable adhesive 118.

FIG. 6 is a cross-sectional view showing the middle and outer tubes 114 and 116 connected together using various weld configurations 120, 122 and 124.

FIG. 7 is a perspective view showing a two-layer tubular assembly 200 according to the present invention where both the inner and outer tubes 212 and 214 have a thinner wall thickness than the prior art monolithic tube 10 shown in FIG. 1.

The present invention will now be described in connection with preferred embodiments, however, it is understood that there is no intent to limit the invention to the embodiments described. On the contrary, the intent is to cover all alternatives, modifications, and equivalents as may be included within the scope of the invention as defined by the appended claims.

DETAILED DESCRIPTION OF THE PREFERRED EMBODIMENTS

As used in this specification, the terms "tube" or "tubular" are defined as a hollow, cylindrical body of metal. The inner tube in the present invention contains the stationary media as the flowing media moves through it. The middle and outer tubes house the inner and middle tubes, respectively. In an alternate embodiment, the inner tube resides inside the outer tube.

The term "column" is defined as a finished product comprising an inner tube residing inside a middle tube, which inner tube/middle tube subassembly resides inside an outer tube. After this tubular assembly is provided with connection features at or adjacent to its opposed ends, it is a column that is suitable for use in high pressure liquid chromatography (HPLC) for use in analytical separation of molecular mixtures.

Figure 1:
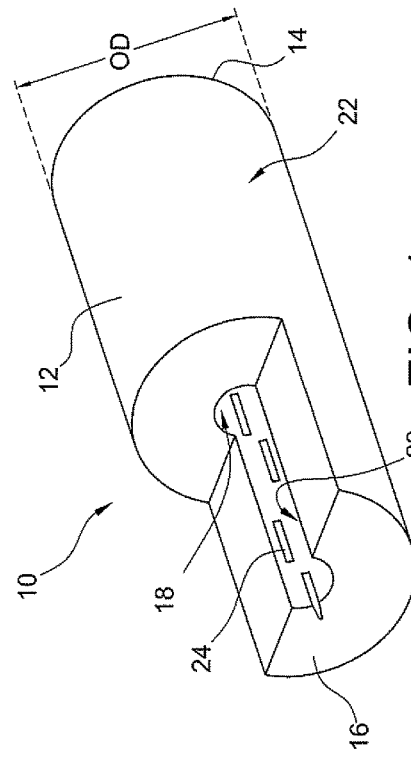
FIG. 1 is perspective view, partly broken away, showing a prior art single layer (monolithic) thick-walled tube 10 with the inner surface presenting typical linear defects 24 that are caused by the drawing process required to produce the monolithic tube.

Turning now to the drawings where like reference numerals indicate like structural elements or process steps, FIG. 1 is a partial cut-away view showing a monolithic heavy or thick-walled tube 10 serving as a high pressure liquid chromatography column according to the prior art. The monolithic tube 10 comprises a sidewall 12 extending axially from a first end 14 to a second end 16. A lumen 18 extending through the tube 10 is defined by a surrounding or annular inner surface 20. The sidewall 12 has an outer diameter (OD) defined by an annular outer surface 22.

Figure 3A:
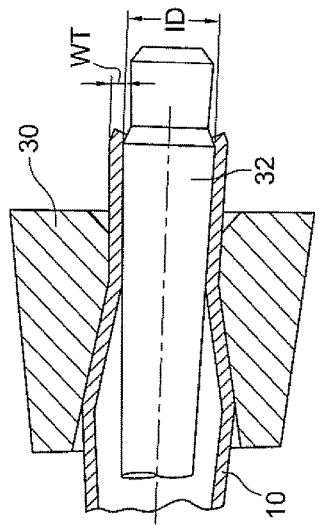
FIG. 3A is a schematic view showing a sink drawing process.
Figure 3B:
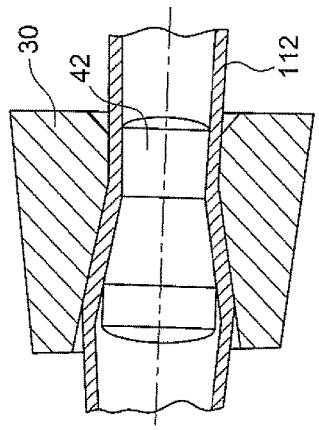
FIG. 3B is a schematic view showing a mandrel drawing process.

Conventional practice is to draw the monolithic thick-walled tube 10 on a straight bench using a combination of sinking, as shown schematically in FIG. 3A, and mandrel drawing, as shown schematically in FIG. 3B. In sink drawing, the tube 10 is pulled through a conical or converging die 30 without any internal tooling. Since the sink drawing process requires no ID tooling, the inner surface 20 remains clean. However, surface roughness and dimensional control of the inner diameter ID are not always optimum, which means secondary mandrel drawing steps are typically needed.

In mandrel drawing, a cylindrical mandrel 32 resides inside the tube 10 at the throat of the die 30. The mandrel 32 exerts a size determination on the wall thickness (WT) and inner diameter (ID). In that respect, mandrel drawing is very useful for providing a wide range of outer diameter to wall thickness ratios (OD:WT). However, a secondary operation is needed to remove the mandrel 32 from the tube 10.

Figure 2:
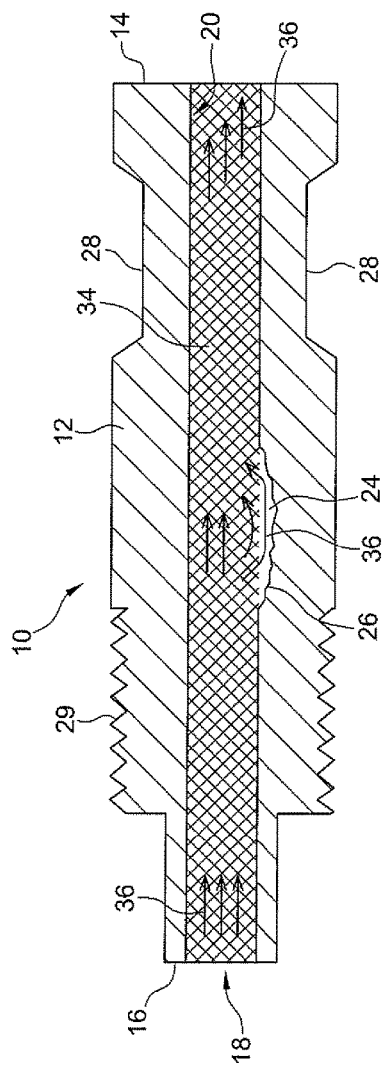
FIG. 2 is a cross-section view of the monolithic tube 10 shown in FIG. 1 including illustrating a flowing media 36 bypassing the stationary media 34 as it flows through a surface defect 24.

For example, a column made from a monolithic tube 10 (FIG. 1) having a 0.250 inch outer diameter and a 0.040 inch inner diameter requires a disproportionate number of sinking draws. As shown in FIGS. 1 and 2, excessive sinking draws are known to result in inner diameter surface defects 24 such as excessive roughness (greater than 32 micro inch Ra) with micro cracks 26 in the trough of the defect 24. If steps are taken in an attempt to smooth out the inner surface defects 24, such as by ironing the inner diameter on a smooth mandrel 32 (FIG. 3B), the micro cracking can become more pronounced. Moreover, withdrawing the mandrel 32 subsequent to the last draw typically introduces additional surface defects. The withdrawal process requires increasing the inner diameter size to loosen the mandrel 32.

To illustrate the undesirability of the prior art monolithic tube 10, the latest generation of a chromatography column has a 0.250 inch OD, a 1 mm (0.040 inch) ID, and a 0.105 inch wall thickness (WT) meaning this design has an OD/WT ratio of only 2.38. As a point of reference, a bar having no ID has an effective OD/WT ratio of 2. Due to the complexities of tube drawing such as for manufacturing a tube having a low OD/WT ratio of below 2.5, it is very difficult and prohibitively expensive to achieve the required smooth, defect-free inner surface required to make an efficient column.

In that respect, FIG. 2 illustrates the prior art monolithic tube 10 configured as a high pressure liquid chromatography column. The tube 10 is provided with connection features adjacent to its first and second ends 14, 16. The depicted connection features are exemplary and include wrench or machine flats 28 adjacent to the first end 14 and screw threads 29 adjacent to the second end 16. The connection features 28, 29 provide for connecting the tube 10 to chromatography equipment and a pressurized sample of solvent and analyte to be analyzed.

A packing material or stationary media 34 of very small spheres (represented by the indicated cross-hatching) is filled into the lumen 18 of the column 10. It is apparent that the stationary media 34 has not completely filled into the surface defect 24 including its micro crack 26. This is undesirable since during an analytical chromatography process, the liquid sample, represented by the arrows 36, flows through the defect 24 and micro crack 26, bypassing the stationary media 34. This has the result of broadening the sample peak at the chromatography detector.

Thus and as previously discussed, the current trend is to smaller and smaller inner diameters in high pressure liquid chromatography columns, but without the presence of undesirable surface defects in the inner surface or inner diameter. This trend is driven by the analytical industry's need to separate smaller sample quantities and to improve separation selectively.

Turning now to the present invention, FIG. 4 is a partial cut-away view showing a novel multi-layer composite tubular assembly 100. The tubular assembly 100 comprises an inner tube 112, a middle tube 114, and an outer tube 116. A significant aspect of the present invention is that the two outer tubes 114 and 116 are made using the fixed plug drawing process depicted in FIG. 3C while the inner tube 112 is made using the floating plug drawing process depicted in FIG. 3D. Since it is not critical that the middle and outer tubes 114, 116 have inner diameters with smooth surfaces and that adhere to strict dimensional tolerances, the fixed plug drawing process is acceptable.

Moreover, the outer diameter to wall thickness (OD:WT) ratios for each of the inner, middle and outer tubes 112, 114, 116 does not need to be as low, i.e., below about 3.0, as that of the prior art monolithic tube 10 shown in FIG. 1. Because each tube 112, 114 and 116 represents only a portion of the total wall thickness, the various OD/WT ratios of the tube outer diameter to the tube wall thickness to are in a range of 3.5:1 to 6:1. This decreases the amount of sinking required, thereby improving the smoothness of the respective inner surfaces, particularly that of the inner tube 112 where the formation of surface defects that are so common to the prior art monolithic tube 10 are significantly reduced. Units for surface roughness include micro inches or micrometers followed by a descriptor that defines how the peaks are averaged, either Ra (R=roughness, a=arithmetic) or Rms (rout mean square averaging).

Figure 3C:
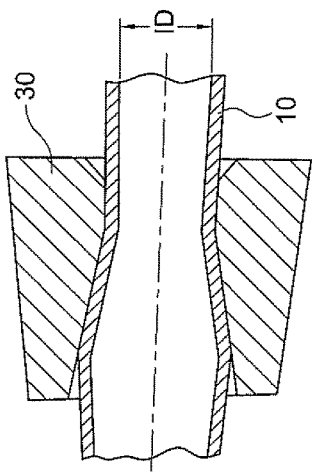
FIG. 3C is a schematic view showing a fixed plug drawing process.

As depicted in FIG. 3C, the fixed plug drawing process, which is also known as stationary mandrel drawing, uses a mandrel 40 at the end of the die 30 to shape the ID of the tube 114, 116. This process is known to produce a very smooth inner surface finish.

Figure 3D:
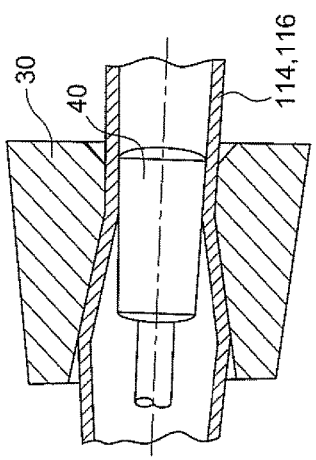
FIG. 3D is a schematic view showing a floating plug drawing process.

As depicted in FIG. 3D, the floating plug drawing process, which is also known as floating mandrel drawing, uses an unanchored mandrel 42 to shape the ID of the inner tube 112. The mandrel 42 is held in the die 30 by the friction forces between the mandrel 42 and the tube 112. Advantages of the floating mandrel process are that it provides desirable dimensional control with a relatively smooth inner lumen surface. Surface roughness is typically below 16 micro inch Ra, and preferably less than 10 micro inch Ra. Importantly, the floating plug drawing process is not prone to micro crack formation on the inner surface 112A of the lumen 112B of the inner tube 112, and a mandrel removal step that could potentially produce scratches and change the tube size is not needed. Moreover, this process can be used on extremely long lengths of tube, such as tube stock in coil form. The inner lumen 112B preferably has a range from about 0.3 mm to about 1.5 mm.

An additional benefit attributed to the use of a separate inner tube 112 in the multi-layer composite tubular assembly 100 according to the present invention is that the inner tube represents a relatively small percent of the total tubular metal content (percent of the assembly weight). This allows for the use of higher cost materials for the inner tube 112 where such high cost materials provide better passivity (inertness or corrosion resistance) and are prone to contain fewer internal defects such as pits and asperities in the finished inner surface. The outer and middle tubes 114, 116 by comparison do not interface with the chromatographic process and may be made from lower cost materials than is desired for the inner tube 112. From an economic perspective, the composite tubular assembly 100 represents a higher cost than the prior art monolithic tube 10 made from 316 stainless steel. However, the improved chromatography performance resulting from use of an inert alloy for the inner tube 112 and having a relatively smooth inner surface allows for a premium product.

The individually produced tubes 112, 114 and 116 are then inserted one inside the other. That is the inner tube 112 is inserted into the lumen 114A of the middle tube 114. Then, the subassembly of the inner and middle tubes 112, 114 is inserted into the lumen 116A of the outer tube 116. Alternatively, the middle tube 114 is inserted into the lumen 116A of the outer tube 116. Then, the inner tube 112 is inserted into the lumen 114A of the subassembly of the outer and middles tubes 114, 116. In any event, the inner, middle and outer tubes of the resulting multi-layer composite tubular assembly 100 are cinched together to a desired finished outer diameter OD size.

Cinching is the process used to reduce the outer diameter of the tubular assembly to the customer size and to bring the tubes in a snug-fit contact relationship with each other. The process is performed by mandrel drawing the assembly. The conical die reduces the tubular assembly until the tubes are in contact with each other. The drawing process then further reduces the assembly until the ID surface of the inner tube contacts the mandrel. After cinch drawing, the mandrel is withdrawn and the tubes are held together by the physical contact between them. The assembly is often referred to as mechanically bonded. After cinching, a first end of the inner tube first end, a first end of the middle tube and a first end of the outer tube first end are substantially coplanar. Further, a second end of the and wherein the inner tube second end, the middle tube second end and the outer tube second end are substantially coplanar.

FIG. 5 illustrates an alternate embodiment for joining the inner, middle and outer tubes 112, 114 and 116 together. A thermosetting adhesive 118 is introduced between the inner and middle tubes 112, 114, and between the middle and outer tubes 114, 116. The assembly is cinched together and then heated to set the adhesive 118. Suitable thermosetting adhesives for metal joining include Phenolic formaldehyde (PF) distributed by Williams-Hayward Protective Coatings, Inc., Summit Ill., polyimides, and epoxies.

FIG. 6 illustrates another embodiment for joining the inner, middle and outer tubes 112, 114 and 116 together using welds. As shown, welds join the outer tube 116 to the middle tube 114. The welds can be any one of an annular weld 120, a spot weld 122, or an axial weld 124 that run along the length of the tubes, and combinations therefore. Regardless the shape of the weld, however, it should not penetrate to the inner tube 112. If it did, there would be concern that the heat of weld formation would adversely affect the smoothness of the inner surface 112A. Consequently, in this embodiment the inner tube 112 is joined to the middle tube 114 by cinching or using an adhesive 118. Laser welding is preferred for making the welds 120, 122 and 124.

If desired, one of the middle and outer tubes 114 and 116 is eliminated. However, the inner tube 112 is maintained as an important component of a two-tube composite assembly 200 according to the present invention. An exemplary two-tube assembly 200 is illustrated in FIG. 7 and comprises an inner tube 212 received in the lumen of an outer tube 214. In a similar manner as with the three-tube composite assembly 100 shown in FIG. 4, the inner tube 212 is made by the floating plug drawing process depicted in FIG. 3D and the outer tube 214 is made by the fixed plug drawing process depicted in FIG. 3C. The inner and outer tubes 212 and 214 are then mechanically cinched together or joined using an adhesive 118 as shown in FIG. 5.

The three-layer tubular assembly 100 (FIG. 4), or two-layer tubular assembly 200 (FIG. 5) are then machined to have connection features adjacent to their opposed ends. Exemplary connection feature are depicted in FIG. 2 and include wrench or machine flats 28 and screw threads 29, or a combination thereof. The flats 28 and screw threads 29 are configured for connection of the tubular assemblies 100, 200 to the chromatography equipment and a pressurized sample of solvent and analyte to be analyzed.

Grade 316 stainless steel is typically specified for inner tubes 112 and 212 with ID surface having a smoothness that is measure as being 10 micro inch Ra or less, but greater than zero, with no interruptions or surface defects such as scratches, pits, or asperities.

Since the present invention columns are designed to be attached to the sample flow path of a chromatographic equipment using standard (US) or metric threads and fittings, the column outer diameter (OD) is fixed while the inner diameter (ID) varies with the desired chromatographic conditions. Standard ¼ inch OD columns are now being specified with inner diameters of 1 mm (about 0.040 inch), and below. In contrast, conventional monolithic columns 10 as shown in FIGS. 1 and 2 are typically provided with inner diameters down to about 2.1 mm (about 0.083 inches). Column lengths range from about ½ inch to about 5 inches.

Accordingly, a multi-layer tubular structure 100, 200 according to the present invention desirable has the following functions:

A. a corrosion resistant OD surface that can withstand the general laboratory environment;

B. sufficient thickness, machinability, and strength that is suitable for machining connection features such as threads and wrenching flats on the OD surface;

C. sufficient strength to contain the very high hydrostatic pressures required for packing the stationary phase media and for withstanding high pressure sample flow therethrough during the analytical separation process;

D. a passive, defect free ID surface that will not react with the solvent or analyte during the separation process or that will not permit the analyte to bypass the stationary media through linear defects; and E. a cost of manufacture that is consistent with the value of the analytical process.

In the three-tube composite column 100 shown in FIG. 4, the outer tube 116 provides the above functions A and B. The middle and outer tubes 114, 116 combine to provide function C, while the inner tube 112 provides function D. All three-tubes combine to determine overall cost (function E). The materials of each tubular layer can be chosen independently. For example, in the three-tube design, the inner tube 112 only provides function D. Therefore, the material of the inner tube is selected to maximize function D as long as that tube is thin so that its contribution to the cost of the finished column 100 does not compromise function E.

In the two-tube composite tubular assembly 200 shown in FIG. 7, the outer tube 214 provides the above functions A and B. The inner tube 212 and outer tube 214 combine to provide functions C and E, while the inner tube 212 provides function D. Again the materials of each tubular layer can be chosen independently.

Exemplary Embodiments

In one embodiment of the present invention, a two-tube composite column has a low cost 304 stainless steel outer tube and a higher cost, more corrosion resistant 316 stainless steel inner tube. In comparison to the prior art monolithic column tube 10 illustrated in FIGS. 1 and 2, the material cost of the resulting HPLC column is reduced without compromising functionality.

In another embodiment, a two-tube composite column has a high strength 17-7PH stainless steel outer tube and a 316 stainless steel inner tube. The resulting HPLC column has a relatively higher resistance to high hydrostatic packing and HPLC sample flow pressures than the conventional prior art monolithic column 10 of a similar composite wall thickness, or similar resistance at a lesser wall thickness.

In a further embodiment, a three-tube composite column has a 304 stainless steel outer tube, a 17-7PH stainless steel middle tube, and a relatively thin 316LVM inner tube.

In yet another embodiment, a three-tube composite column has a relatively low cost 304 stainless steel outer tube, a high strength 17-7PH stainless steel middle tube, and a thin, commercially pure titanium inner tube. The resulting HPLC column has acceptable resistance to hydrostatic pressures up to at least 20,000 psi, and a passive inner surface compatible with biologic analysis.

In yet another embodiment, a three-tube composite column comprises a relatively low cost 304 stainless steel outer tube, a high strength 17-7PH stainless steel middle tube, and a thin, commercially pure titanium inner tube as described in the previous embodiment, but is provided with a heat setting polymer adhesive between the outer and middle tubes and between middle and inner tubes. A post assembly heat treatment process is applied to harden the polymer adhesives, thereby producing an assembly with stronger bonding between the tubes than would be achieved with only a mechanical bond resulting from cinching the tubes after assembly.

In yet another embodiment, a three-tube composite column comprises a relatively low cost 304 stainless steel outer tube, a high strength 17-7PH stainless steel middle tube, and a thin, commercially pure titanium inner tube as described in the previous embodiment, but using laser welds to connect the outer and middle tubes. There are a series of radial welds, spot welds, or axial welds, and combinations thereof that penetrate through the outer tube and into the middle tube, but do not penetrate the inner tube. The laser welds produce an assembly with stronger bonding between the tubes than is achieved with only the mechanical bond resulting from cinching the tubes after assembly.

Although several embodiments of the invention have been described in detail, for purposes of illustration, various modifications of each may be made without departing from the spirit and scope of the invention. Accordingly, the invention is not to be limited, except as by the appended claims.

What is claimed is:

1. A chromatography column, which comprises:
   a) an inner tube comprising an outer surface having an inner tube outer diameter extending along a longitudinal axis to spaced apart inner tube first and second ends, wherein an inner lumen defined by an inner tube inner annular surface has an inner diameter that extends through the inner tube to the inner tube first and second ends, the inner tube inner annular surface being devoid of interruptions with a surface roughness that is greater than zero, but equal to or less than 16 micro inch Ra;
   b) a middle tube comprising an outer surface having a middle tube outer diameter extending along the longitudinal axis to spaced apart middle tube first and second ends, wherein a middle lumen defined by a middle tube inner annular surface has an inner diameter that extends through the middle tube to the middle tube first and second ends; and
   c) an outer tube comprising an outer surface having an outer tube outer diameter extending along the longitudinal axis to spaced apart outer tube first and second ends, wherein an outer lumen defined by an outer tube inner annular surface has an inner diameter that extends through the outer tube to the outer tube first and second ends,
   d) wherein the middle lumen through the middle tube is sized to receive the annular outer surface of the inner tube in a first snug-fit relationship, and wherein the outer lumen through the outer tube is sized to receive the annular outer surface of the middle tube in a second snug-fit relationship so that the inner tube resides inside and is contacted by the middle tube and the middle tube resides inside and is contacted by the outer tube, and
   e) wherein the inner, middle and outer tubes are selected from the group consisting of 304 stainless steel, 316 stainless steel, 316 LVM stainless steel, 17-7PH stainless steel, and titanium.

2. The chromatography column of claim 1, wherein the inner tube is characterized as having been connected to the middle tube and middle tube is characterized as having been connected to the outer tube by a cinching process.

3. The chromatography column of claim 1, wherein the inner tube is connected to the middle tube and the middle tube is connected to the outer tube by a thermal-setting adhesive.

4. The chromatography column of claim 1, wherein the inner tube is characterized as having been connected to the middle tube by a cinching process and the middle tube is welded to the outer tube.

5. The chromatography column of claim 1, wherein the inner tube is connected to the middle tube by a thermal-setting adhesive and the middle tube is welded to the outer tube.

6. The chromatography column of claim 1, wherein the outer tube is configured for connection to other chromatography equipment.

7. The chromatography column of claim 1, wherein:
   a) the inner tube has an inner tube wall thickness measured between the inner tube inner annular surface and an inner tube outer diameter, and a ratio of the inner tube outer diameter to the inner tube wall thickness (OD:WT) is in a range of 3.5:1 to 6:1;
   b) the middle tube has a middle tube wall thickness measured between the middle tube inner annular surface and a middle tube outer diameter, and a ratio of the middle tube outer diameter to the middle tube wall thickness is in a range of 3.5:1 to 6:1; and
   c) the outer tube has an outer tube wall thickness measured between the outer tube inner annular surface and an outer tube outer diameter, and a ratio of the outer tube outer diameter to the outer tube wall thickness is in a range of 3.5:1 to 6:1.

8. The chromatography column of claim 1, wherein the inner lumen of the inner tube has an inner tube inner diameter that ranges from 0.3 mm to 1.5 mm.

9. The chromatography column of claim 1, wherein the inner annular surface of the inner tube has a continuous surface roughness that is greater than zero, but equal to or less than 10 micro inch Ra.

10. The chromatography column of claim 1, having a length that ranges from ½ inch to 5 inches.

11. The chromatography column of claim 1, wherein the inner tube first end, the middle tube first end and the outer tube first end are substantially coplanar, and wherein the inner tube second end, the middle tube second end and the outer tube second end are substantially coplanar.

12. A method for providing a chromatography column, comprising the steps of:
   a) drawing an inner tube using a floating plug drawing process, the inner tube comprising an inner tube outer surface having an inner tube outer diameter extending along a longitudinal axis to spaced apart inner tube first and second ends, wherein an inner lumen defined by an inner annular surface having an inner diameter extends through the inner tube to the inner tube first and second ends, the inner tube inner diameter being devoid of interruptions with a surface roughness that is greater than zero, but less than 16 micro inch Ra;
   b) drawing a middle tube using a fixed plug drawing process, the middle tube comprising a middle tube outer surface having a middle tube outer diameter extending along the longitudinal axis to spaced apart middle tube first and second ends, wherein a middle lumen defined by a middle tube inner annular surface having an inner diameter extends through the middle tube to the middle tube first and second ends;
   c) drawing an outer tube using a fixed plug drawing process, the outer tube comprising an outer tube outer surface having an outer tube outer diameter extending along the longitudinal axis to spaced apart outer tube first and second ends, wherein an outer lumen defined by an outer tube inner annular surface having an inner diameter extends through the outer tube to the outer tube first and second outer tube ends; and
   d) assembling the inner tube residing inside and contacting the middle tube and the middle tube residing inside and contacting the outer tube to thereby provide the chromatography column, and
   e) wherein the inner, middle and outer tubes are selected from the group consisting of 304 stainless steel, 316 stainless steel, 316 LVM stainless steel, 17-7PH stainless steel, and titanium.

13. The method of claim 12, including cinching the inner tube to the middle tube and cinching the middle tube to the outer tube by a cinching process.

14. The method of claim 12, including connecting the inner tube to the middle tube and connecting the middle tube to the outer tube using a thermal-setting adhesive.

15. The method of claim 12, including providing:
a) the inner tube having an inner tube wall thickness measured between the inner tube inner annular surface and an inner tube outer diameter so that a ratio of the inner tube outer diameter to the inner tube wall thickness (OD:WT) is in a range of 3.5:1 to 6:1;
b) the middle tube having a middle tube wall thickness measured between the middle tube inner annular surface and a middle tube outer diameter so that a ratio of the middle tube outer diameter to the middle tube wall thickness is in a range of 3.5:1 to 6:1; and
c) the outer tube having an outer tube wall thickness measured between the outer tube inner annular surface and an outer tube outer diameter so that a ratio of the outer tube outer diameter to the outer tube wall thickness is in a range of 3.5:1 to 6:1.

16. The method of claim 12, including providing the inner lumen of the inner tube having an inner tube diameter that ranges from 0.3 mm to 1.5 mm.

17. The method of claim 12, including providing the inner surface of the inner tube having a surface roughness that is greater than zero, but equal to or less than 10 micro inch Ra.

18. The method of claim 12, including providing the chromatography column having a length ranging from ½ inch to 5 inches.

19. A chromatography column, which comprises:
a) an inner tube selected from the group consisting of 316 stainless steel, 316 LVM stainless steel, and titanium, the inner tube comprising an outer surface having an inner tube outer diameter extending along a longitudinal axis to spaced apart inner tube first and second ends, wherein an inner lumen defined by an inner tube inner annular surface has an inner diameter that extends through the inner tube to the inner tube first and second ends;
b) a middle tube selected from the group consisting of 304 stainless steel, 316 stainless steel, and 17-7PH stainless steel, the middle tube comprising an outer surface having a middle tube outer diameter extending along the longitudinal axis to spaced apart middle tube first and second ends, wherein a middle lumen defined by a middle tube inner annular surface has an inner diameter that extends through the middle tube to the middle tube first and second ends; and
c) an outer tube selected from 304 stainless steel, 316 stainless steel, and 17-7PH stainless steel, the outer tube comprising an outer surface having an outer tube outer diameter extending along the longitudinal axis to spaced apart outer tube first and second ends, wherein an outer lumen defined by an outer tube inner annular surface has an inner diameter that extends through the outer tube to the outer tube first and second ends,
d) wherein the middle lumen through the middle tube is sized to receive the annular outer surface of the inner tube in a first snug-fit relationship, and wherein the outer lumen through the outer tube is sized to receive the annular outer surface of the middle tube in a second snug-fit relationship so that the inner tube resides inside and is contacted by the middle tube and the middle tube resides inside and is contacted by the outer tube.

20. The chromatography column of claim 19, wherein the inner tube is characterized as having been connected to the middle tube and middle tube is characterized as having been connected to the outer tube by a cinching process.

21. The chromatography column of claim 19, wherein the inner tube is connected to the middle tube and the middle tube is connected to the outer tube by a thermal-setting adhesive.

22. The chromatography column of claim 19, wherein the inner tube is characterized as having been connected to the middle tube by a cinching process and the middle tube is welded to the outer tube.

23. The chromatography column of claim 19, wherein the inner tube is connected to the middle tube by a thermal-setting adhesive and the middle tube is welded to the outer tube.

24. The chromatography column of claim 19, wherein the outer tube is configured for connection to other chromatography equipment.

25. The chromatography column of claim 19, wherein:
a) the inner tube has an inner tube wall thickness measured between the inner tube inner annular surface and an inner tube outer diameter, and a ratio of the inner tube outer diameter to the inner tube wall thickness (OD:WT) is in a range of 3.5:1 to 6:1;
b) the middle tube has a middle tube wall thickness measured between the middle tube inner annular surface and a middle tube outer diameter, and a ratio of the middle tube outer diameter to the middle tube wall thickness is in a range of 3.5:1 to 6:1; and
c) the outer tube has an outer tube wall thickness measured between the outer tube inner annular surface and an outer tube outer diameter, and a ratio of the outer tube outer diameter to the outer tube wall thickness is in a range of 3.5:1 to 6:1.

26. The chromatography column of claim 19, wherein the inner lumen of the inner tube has an inner tube inner diameter that ranges from 0.3 mm to 1.5 mm.

27. The chromatography column of claim 19, wherein the inner annular surface of the inner tube has a continuous surface roughness that is greater than zero, but equal to or less than 16 micro inch Ra.

28. The chromatography column of claim 19, having a length that ranges from ½ inch to 5 inches.

* * * * *